United States Patent [19]

Yamamoto et al.

[11] Patent Number: 5,097,054

[45] Date of Patent: Mar. 17, 1992

[54] PROCESS FOR PRODUCING HYDROGENSILOXANES

[75] Inventors: Yasushi Yamamoto, Takasaki; Takashi Matsuda, Annaka, both of Japan

[73] Assignee: Shin-Etsu Chemical Co., Ltd., Tokyo, Japan

[21] Appl. No.: 633,689

[22] Filed: Dec. 26, 1990

[30] Foreign Application Priority Data

Dec. 27, 1989 [JP] Japan .................................. 1-339792

[51] Int. Cl.$^5$ .............................................. C07F 7/08
[52] U.S. Cl. .................................................... 556/451
[58] Field of Search ......................................... 556/451

[56] References Cited

U.S. PATENT DOCUMENTS

| | | | |
|---|---|---|---|
| 2,877,255 | 3/1959 | Clark | 556/451 |
| 3,576,029 | 4/1971 | Haluska | 556/451 |
| 3,898,256 | 8/1975 | Takaniyawa et al. | 556/451 |
| 4,824,982 | 4/1989 | Vableusieck et al. | 556/451 |
| 5,011,962 | 4/1991 | Staiger et al. | 556/451 X |

FOREIGN PATENT DOCUMENTS 0031791  2/1989  Japan .................................. 556/451

*Primary Examiner*—Paul F. Shaver
*Attorney, Agent, or Firm*—Oblon, Spivak, McClelland, Maier & Neustadt

[57] ABSTRACT

A process for producing a hydrogensiloxane represented by the following general formula:

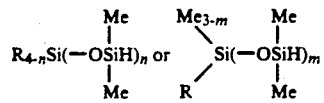

wherein R is a monovalent organic group, Me is the methyl group, n is an integer of 1 to 3, and m is 1 or 2, comprises reacting a chlorosilane represented by the following general formula:

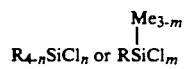

wherein R, Me, n and m are as defined above, with 1,1,3,3-tetramethyldisiloxane in the presence of water and an acid. The process can produce the hydrogensiloxane in a high yield, since side reactions are effectively obviated.

5 Claims, 18 Drawing Sheets

PROCESS FOR PRODUCING HYDROGENSILOXANES

BACKGROUND OF THE INVENTION

1. Field of the Invention

This invention relates to a process for producing a hydrogensiloxane represented by the following general formula (I) or (II):

$$R_{4-n}Si(-OSiH\underset{Me}{\overset{Me}{|}})_n \quad (I)$$

$$\underset{R}{\overset{Me_{3-m}}{\diagdown}}Si(-OSiH\underset{Me}{\overset{Me}{|}})_m \quad (II)$$

wherein R represents a group selected from the group consisting of halogenated hydrocarbon groups, fluorine-substituted ether groups and hydrocarbon groups of at least 2 carbon atoms; and where a plurality of R groups exist, the R's may be either identical or different, Me represents the methyl group, n represents an integer of 1 to 3, and m represents an integer of 1 or 2.

2. Description of the Prior Arts

As a method of producing a hydrogensiloxane represented by the above general formula (I) or (II), methods based on an equilibration reaction of siloxane by use of an acid and methods based on co-hydrolysis of chlorosiloxanes have been known heretofore.

As a method based on the equilibration reaction by use of an acid, for example, there has been known a method of producing the hydrogensiloxane corresponding to m=1 in the above general formula (II) by an equilibration reaction of a siloxane compound represented by the following reaction formula (a):

$$R-\underset{Me}{\overset{Me}{|}}Si-O-\underset{Me}{\overset{Me}{|}}Si-R + H-\underset{Me}{\overset{Me}{|}}Si-O-\underset{Me}{\overset{Me}{|}}Si-H \xrightarrow{\text{acid catalyst}}$$

$$R-\underset{Me}{\overset{Me}{|}}Si-O-\underset{Me}{\overset{Me}{|}}Si-H \quad (a)$$

wherein R and Me are as defined above, and the same meanings will apply in all the formulas where Me appears hereinbelow.

There has been also known a method of producing the hydrogensiloxane corresponding to m=2 in the above general formula (II) by an equilibration reaction of a siloxane compound represented by the following reaction formula (b):

$$\boxed{\left(\underset{R}{\overset{Me}{|}}SiO\right)_a} + H-\underset{Me}{\overset{Me}{|}}Si-O-\underset{Me}{\overset{Me}{|}}Si-H \xrightarrow{\text{acid catalyst}} \quad (b)$$

$$H-\underset{Me}{\overset{Me}{|}}Si(OSi)_b O\underset{Me}{\overset{Me}{|}}Si-H$$

wherein a is an integer of 3 or 4, and b is an integer of 1 or above.

As a method based on co-hydrolysis of chlorosilanes, methods in which a mixture of chlorosilanes represented by $R_{4-n}SiCl_n$ and $HSi(Me)_2Cl$ is brought into co-hydrolysis are described in the following literature:

(A) U.S. Pat. No. 2,877,255
(B) U.S. Pat. No. 2,877,256
(C) R. Okawara, Kogyo Kagaku Zasshi (Journal of the Chemical Society of Japan, Industrial Chemistry Section), 60, 1398 (1957)
(D) R. Okawara, M. Sakiyama, Bull. Chem. Japan, 29, 236 (1956)

However, according to the methods utilizing the equilibration reaction represented by the reaction formula (a) above, the disiloxane used as the starting material is left unreacted, resulting in a considerably low yield of the intended product. According to the methods utilizing the equilibration reaction represented by the above reaction formula (b), on the other hand, polysiloxanes with the number b being 2 or above are by-produced and, therefore, the intended trisiloxane (namely, the hydrogensiloxane corresponding to m=2 in the general formula (II)) cannot always be produced in a satisfactory yield.

Furthermore, the methods by co-hydrolysis of chlorosilanes as described in the above-cited references have the problem that hydrogensiloxanes produced by condensation of a plurality of $R_{4-n}SiCl_n$ molecules would be by-produced.

SUMMARY OF THE INVENTION

It is accordingly an object of this invention to provide a process for producing a hydrogensiloxane represented by the aforementioned general formula (I) or (II) by which the formation of by-products is inhibited effectively and the intended hydrogensiloxane can be produced in a markedly high yield.

According to this invention, there is provided a process for producing a hydrogensiloxane represented by the aforementioned general formula (I), which comprises reacting a chlorosilane represented by the following general formula (III):

$$R_{4-n}SiCl_n \quad (III)$$

wherein R and n are as defined above, with 1,1,3,3-tetramethyldisiloxane in the presence of water and an acid at a temperature of 30° C. or below.

According to this invention, there is also provided a process for producing a hydrogensiloxane represented by the aforementioned general formula (II), which comprises reacting a chlorosilane represented by the following general formula (IV):

$$\underset{RSiCl_m}{Me_{3-m}} \quad (IV)$$

wherein Me, R and m are as defined above, with 1,1,3,3-tetramethyldisiloxane in the presence of water and an acid at a temperature of 30° C. or below.

When any of the processes as aforementioned is employed, the reaction between the silanol, formed through the hydrolysis of the chlorosilane, and the 1,1,3,3-tetramethyldisiloxane proceeds extremely rapidly, to yield the intended hydrogensiloxane. As a result, the condensation reaction between the silanol molecules as well as the equilibration reaction of the hydrogensiloxane formed is obviated effectively, whereby the intended hydrogensiloxane is obtained in a remarkably high yield.

At present, industrial production of dimethylchlorosilane is being carried out by use of 1,1,3,3-tetramethyldisiloxane as a starting material. Therefore, the process of this invention, in which 1,1,3,3-tetramethyldisiloxane is used, is extremely profitable on an industrial basis as compared with the conventional methods in which dimethylchlorosilane is used.

DETAILED DESCRIPTION OF PREFERRED EMBODIMENTS

Starting Material Compounds

Figure 1:
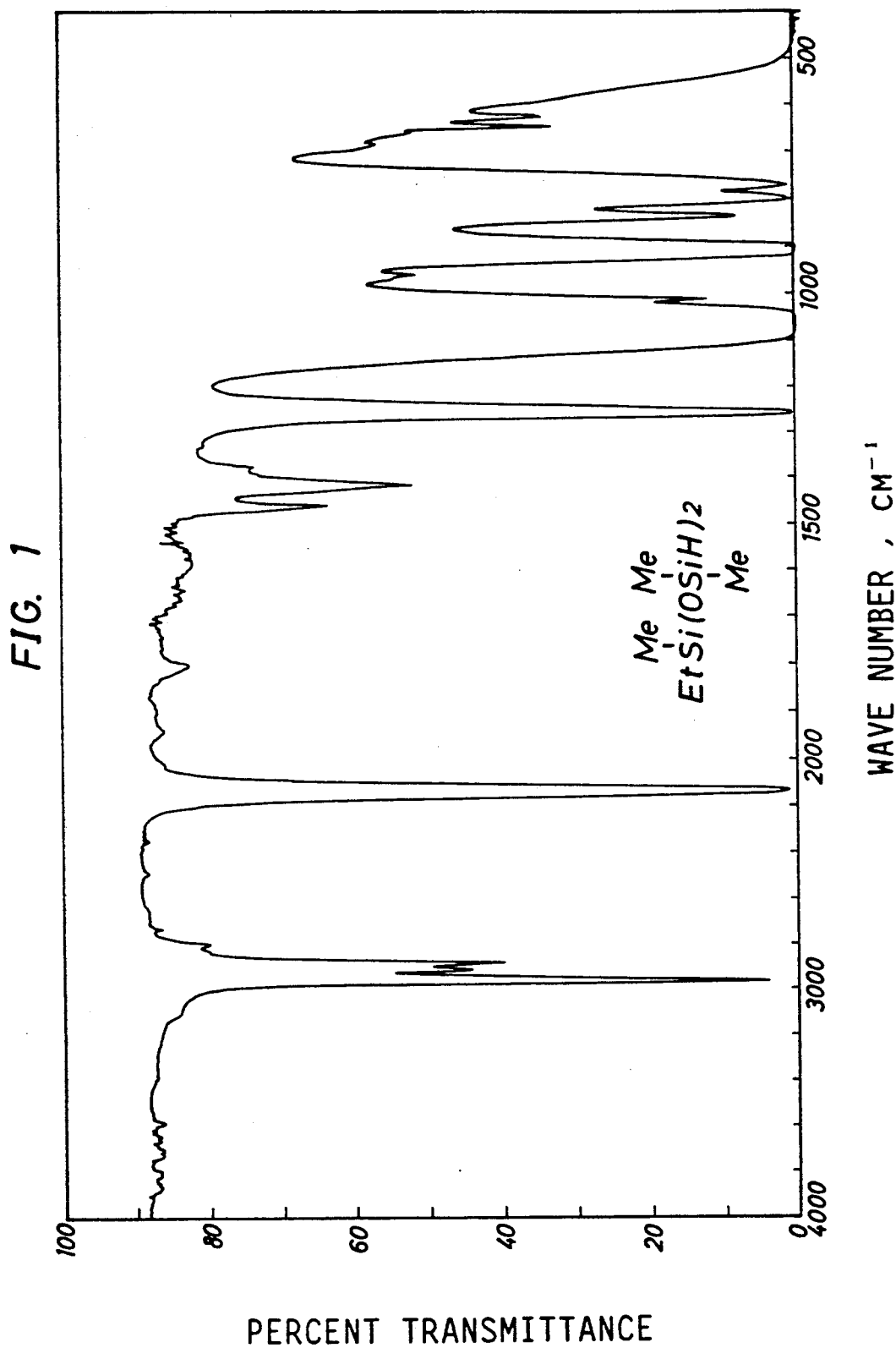
FIGS. 1 to 18 respectively show infrared absorption spectra of hydrogensiloxanes obtained in Examples 1 to 18 which will be described below.
Figure 2:
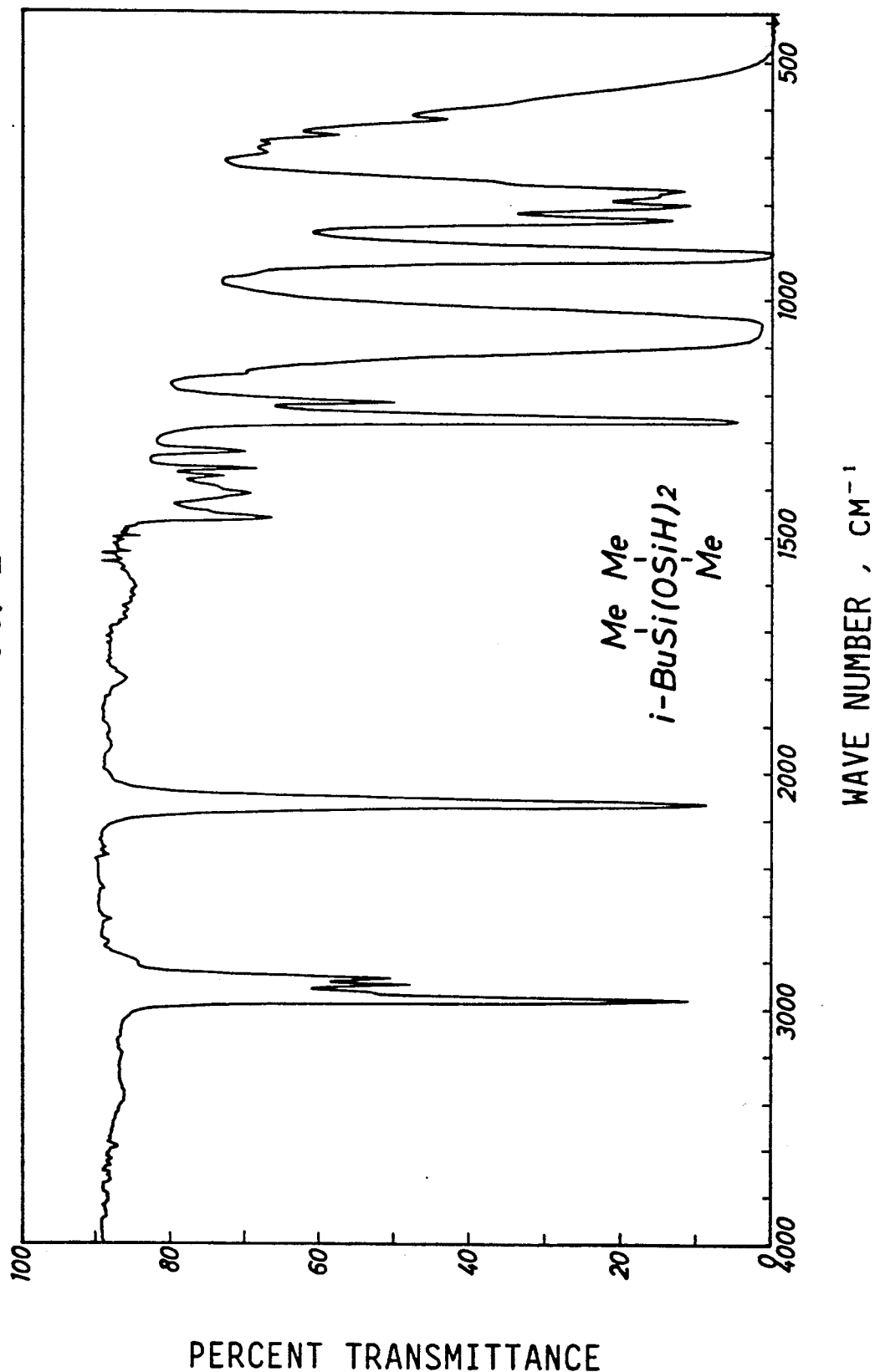
Figure 3:
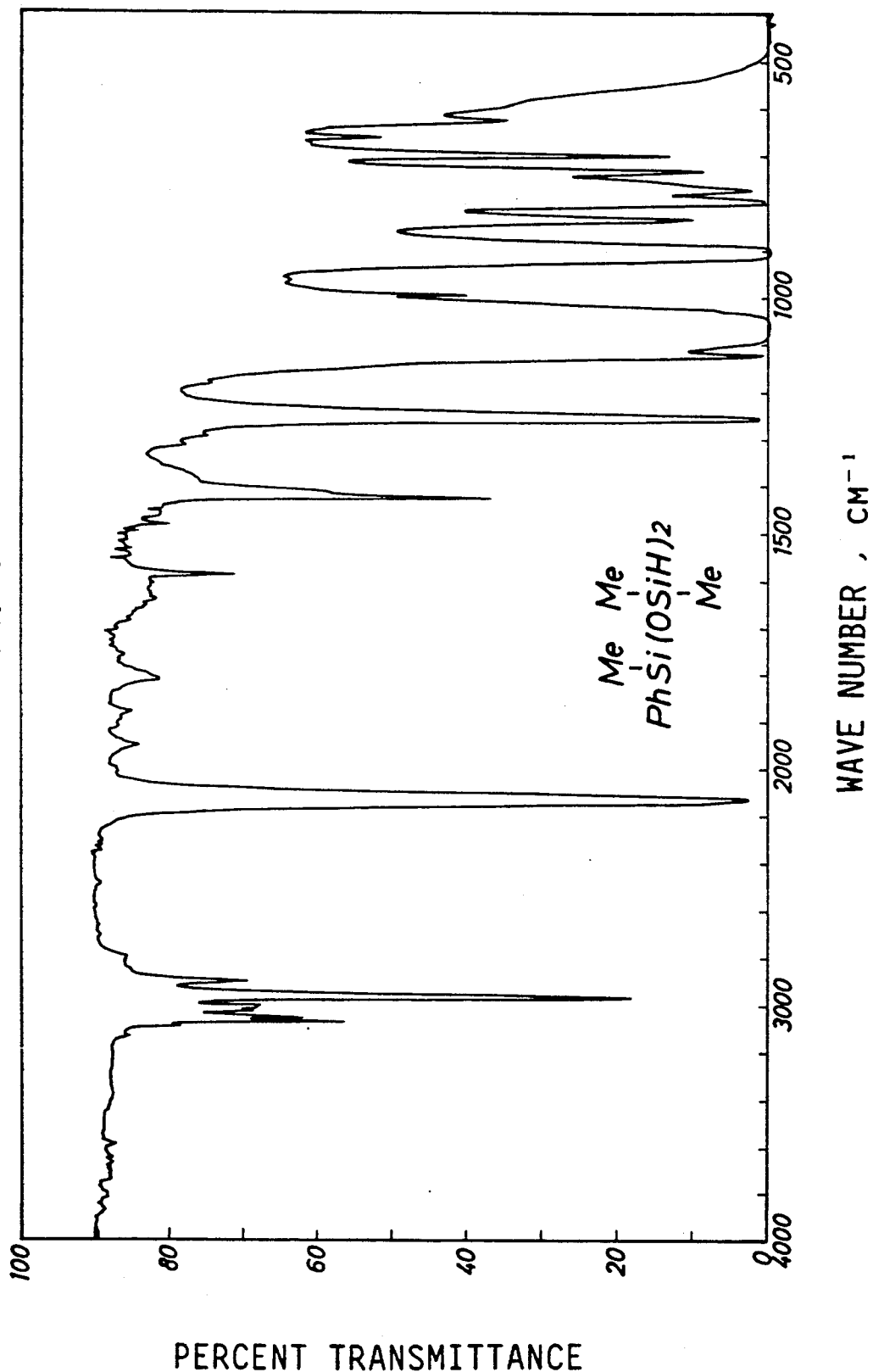
Figure 4:
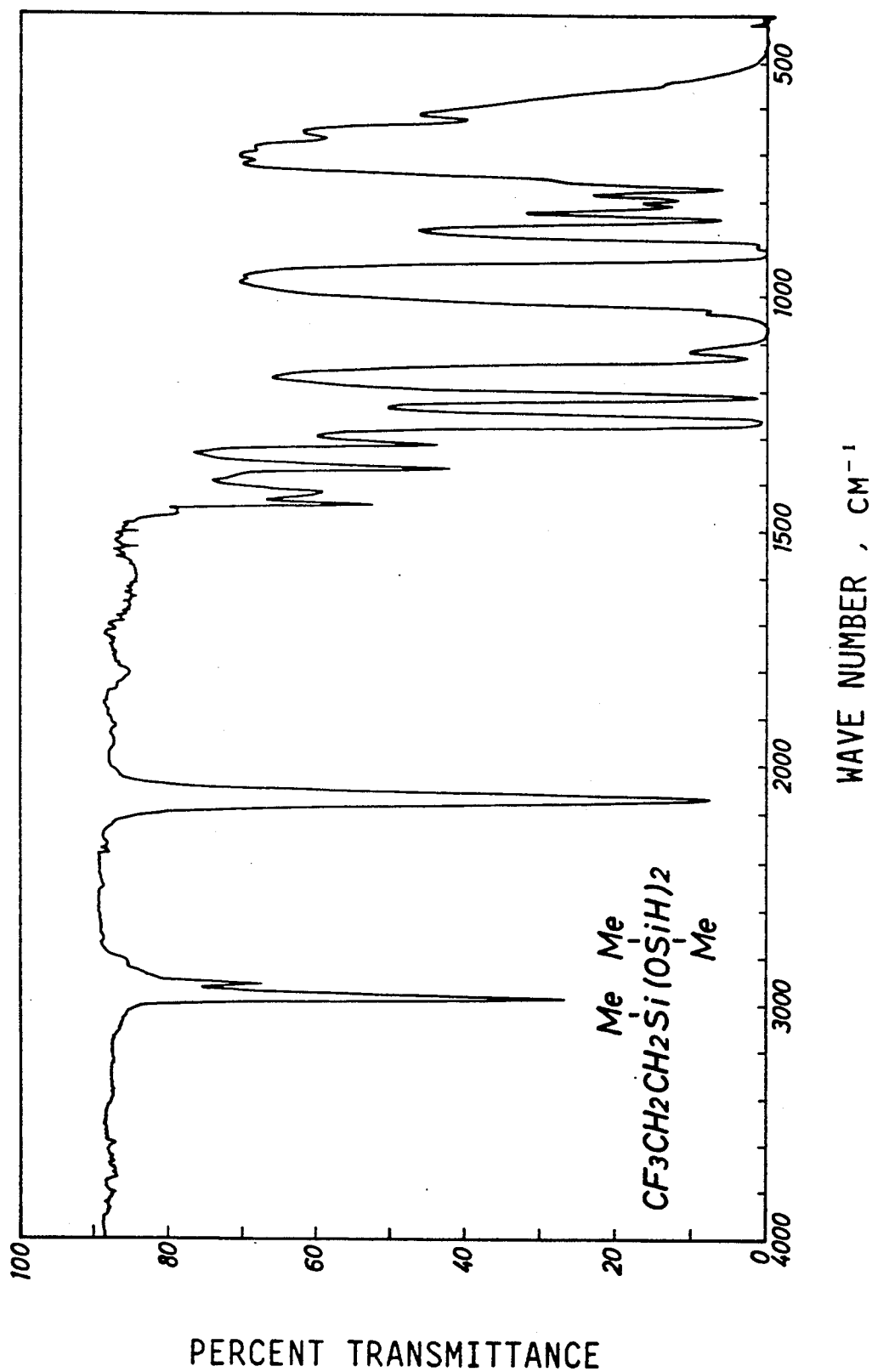
Figure 5:
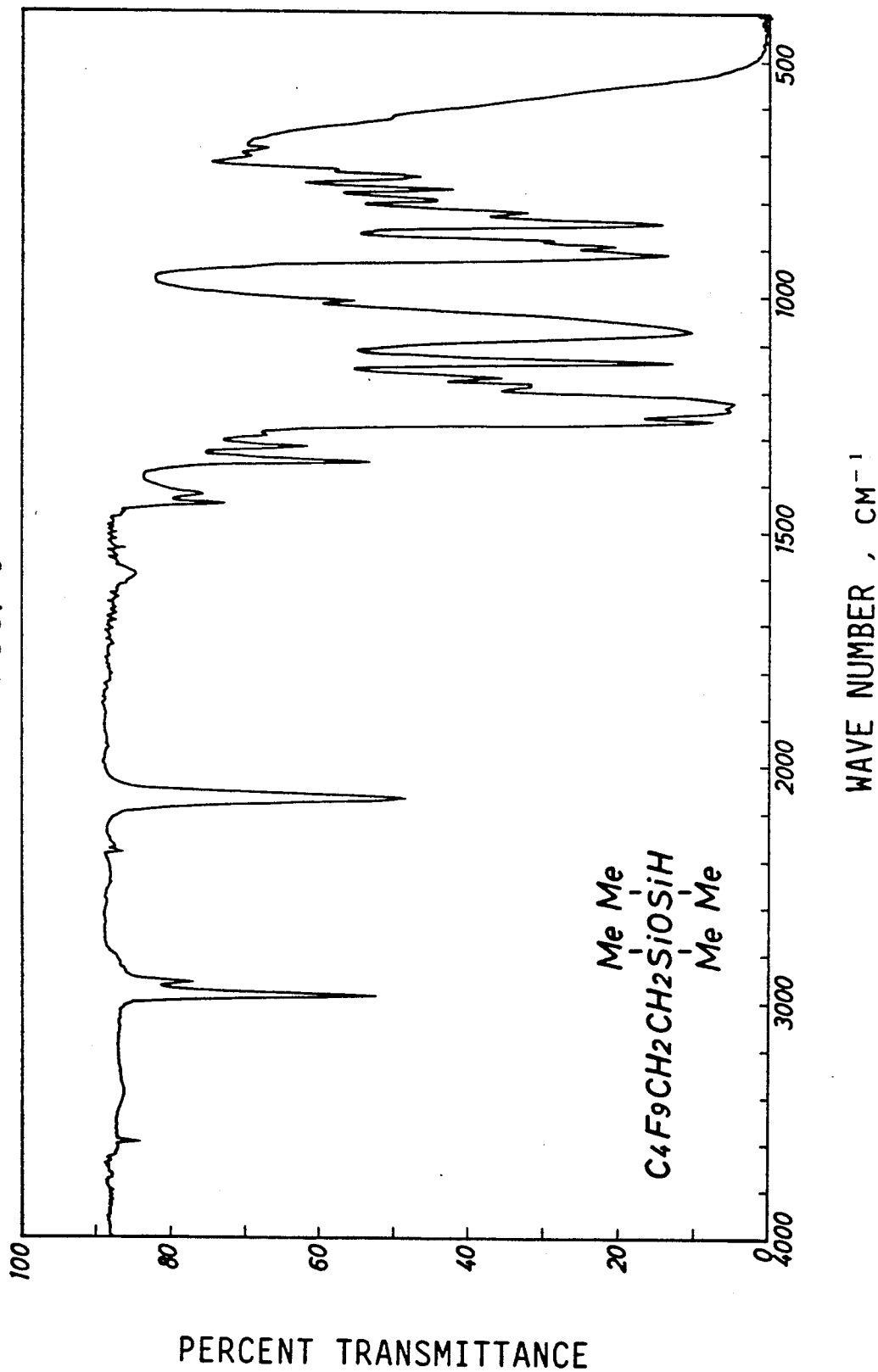
Figure 6:
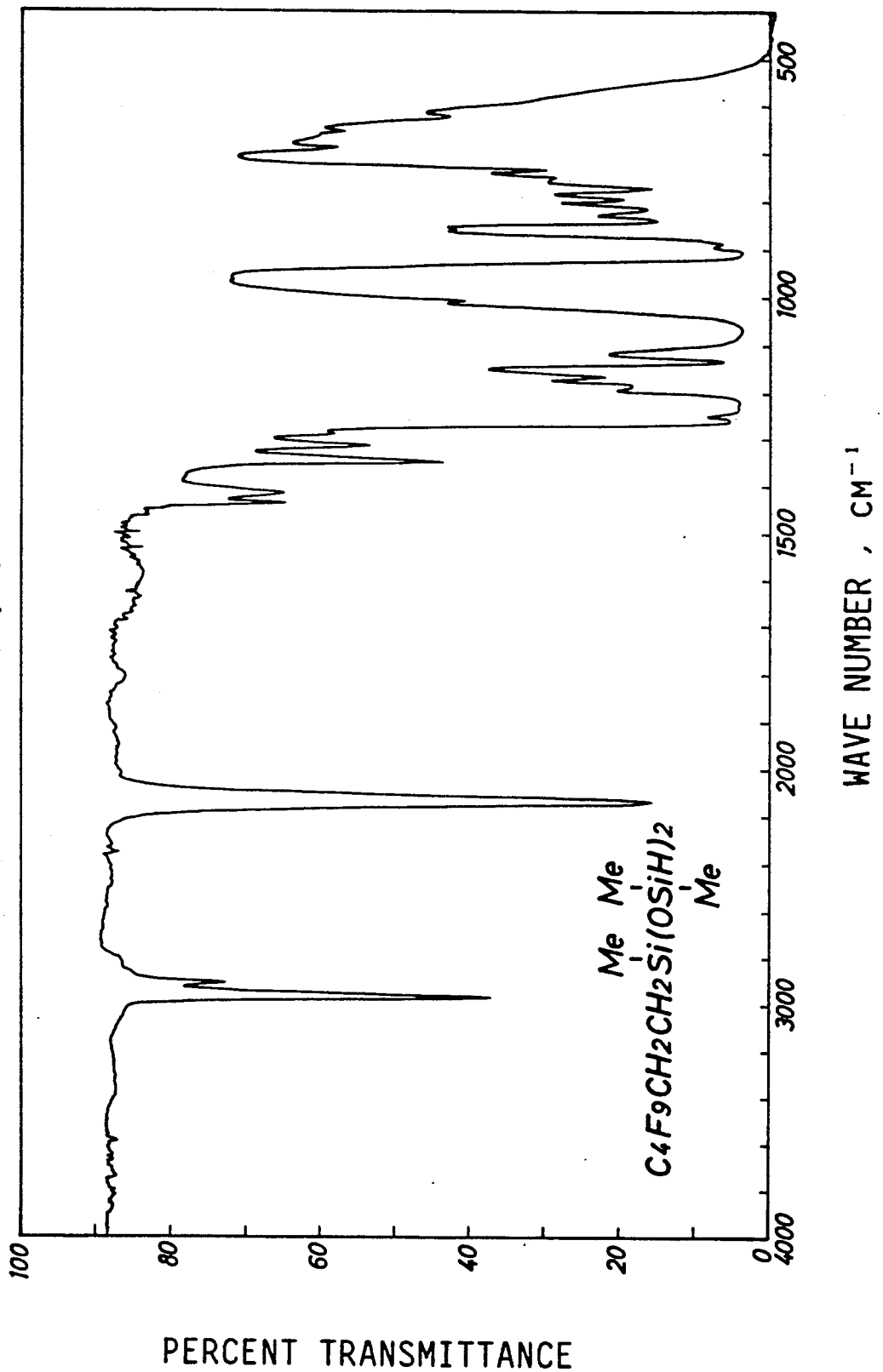
Figure 7:
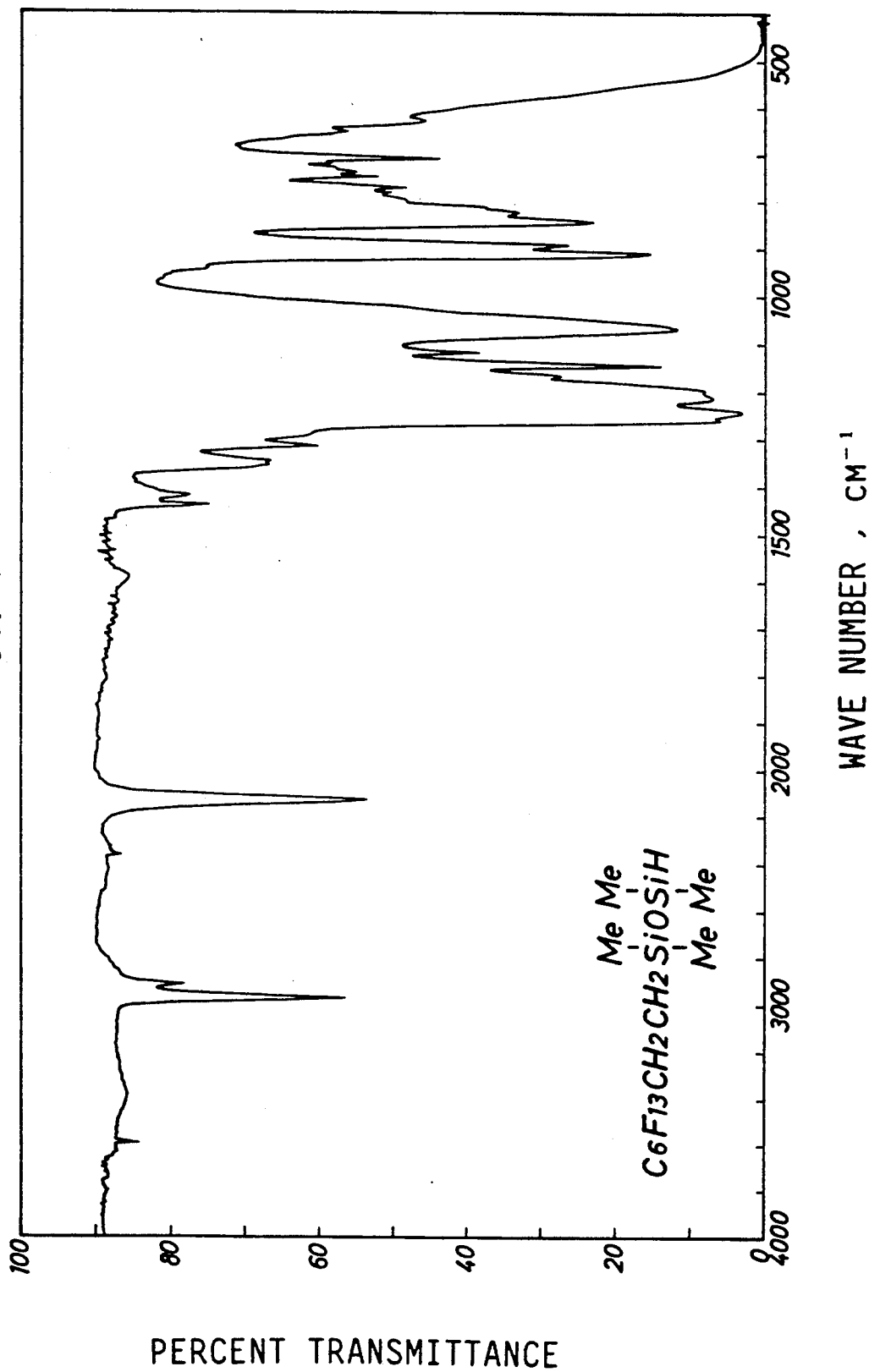
Figure 8:
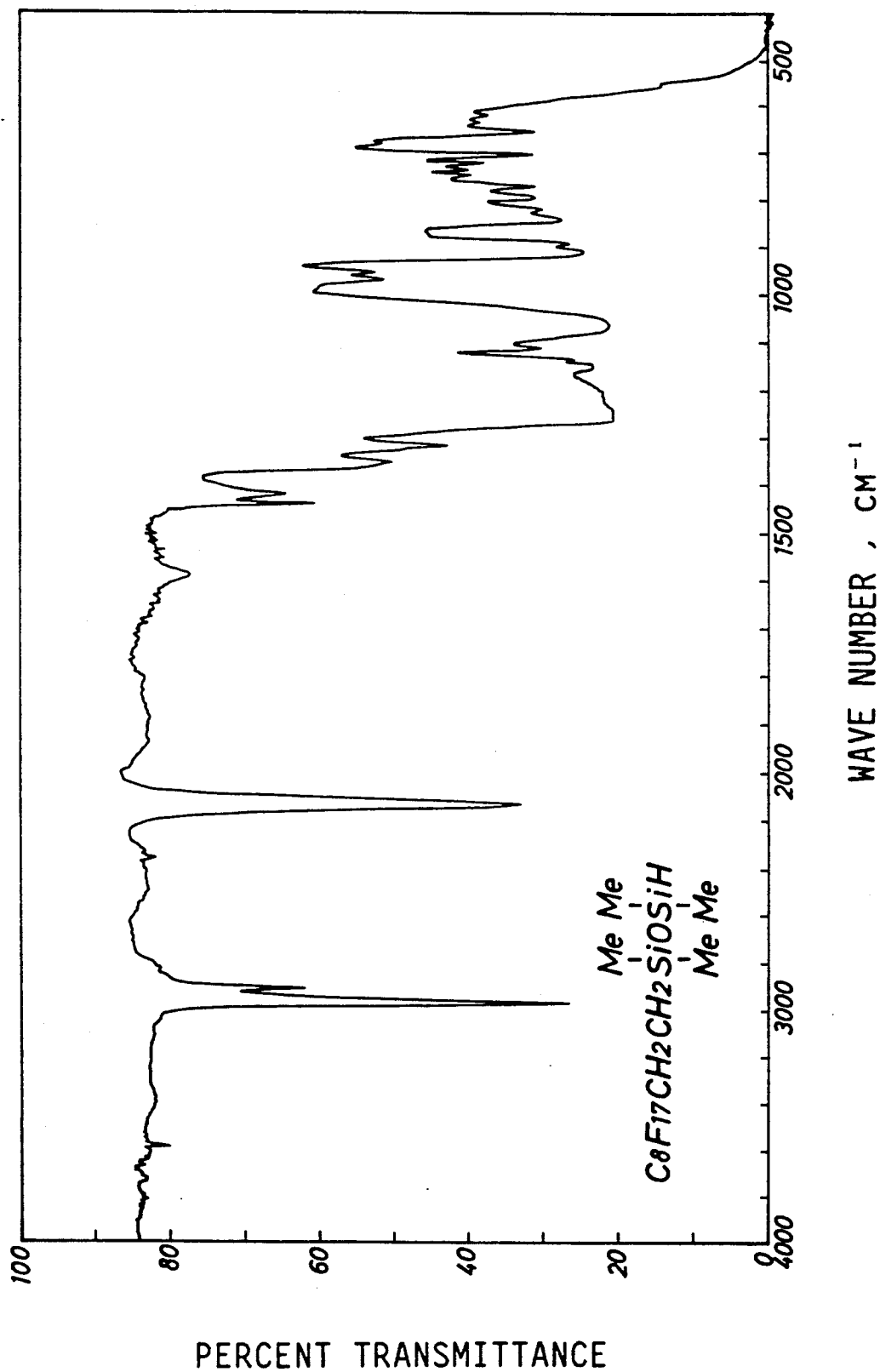
Figure 9:
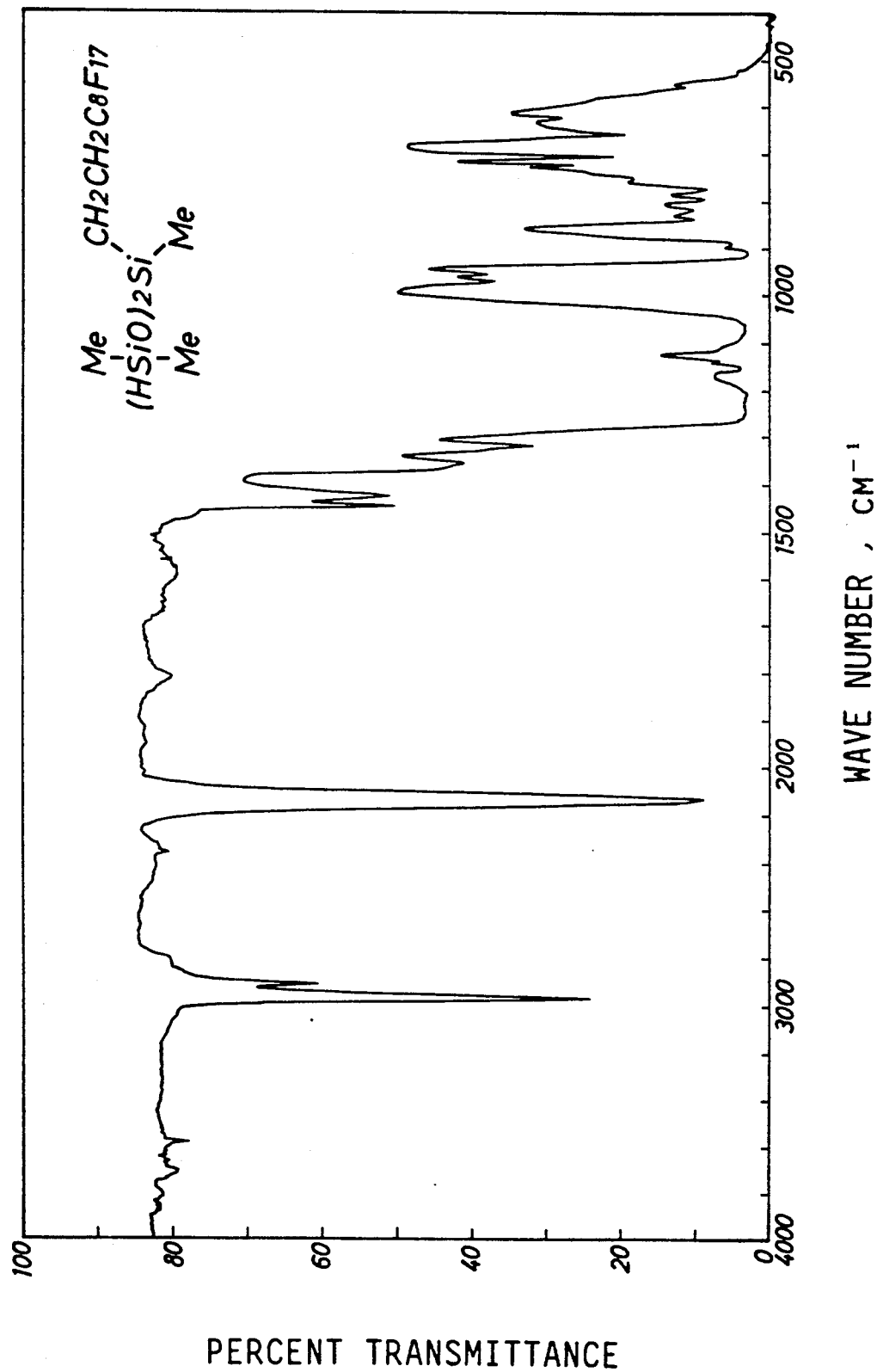
Figure 10:
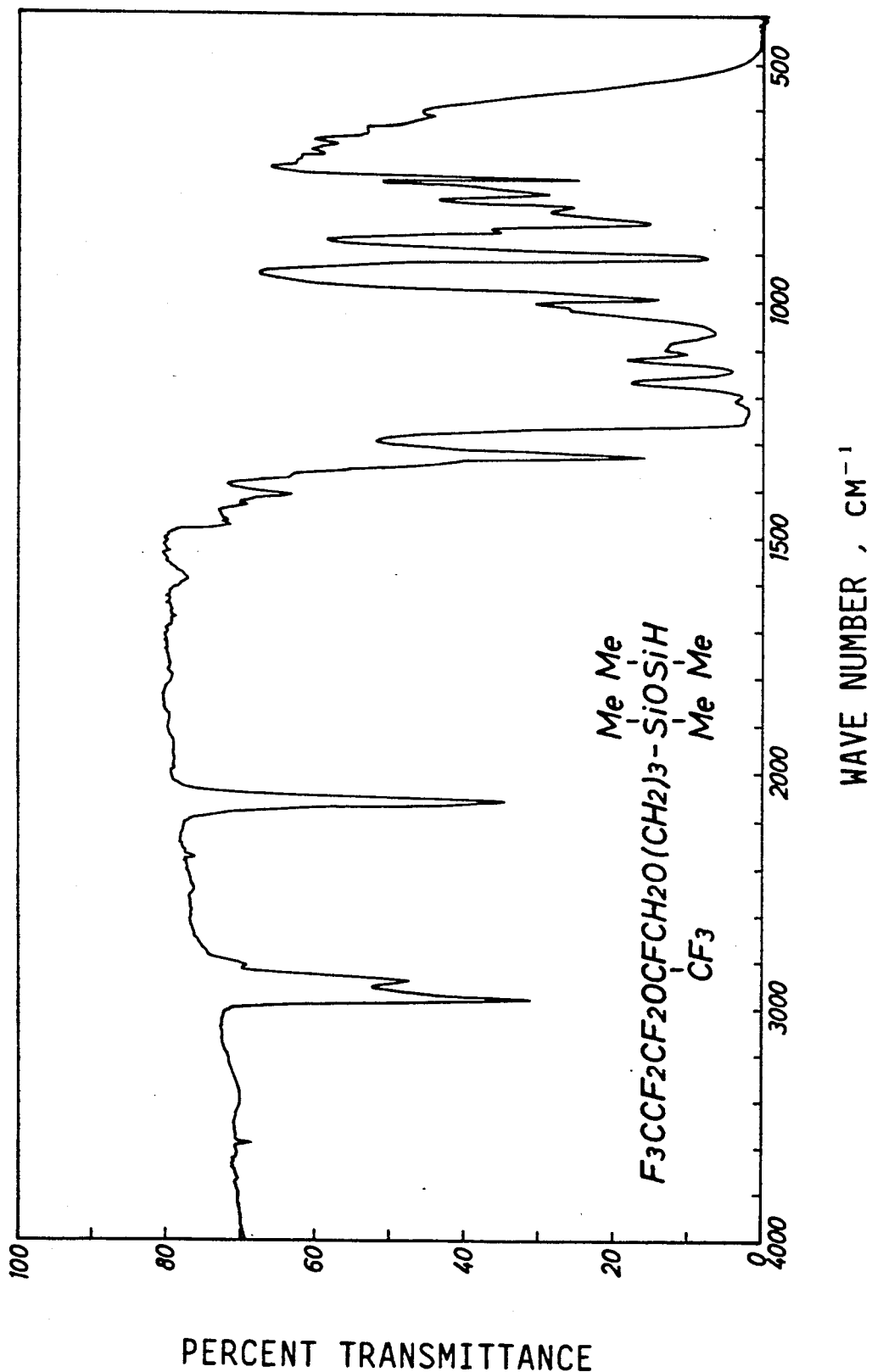
Figure 11:
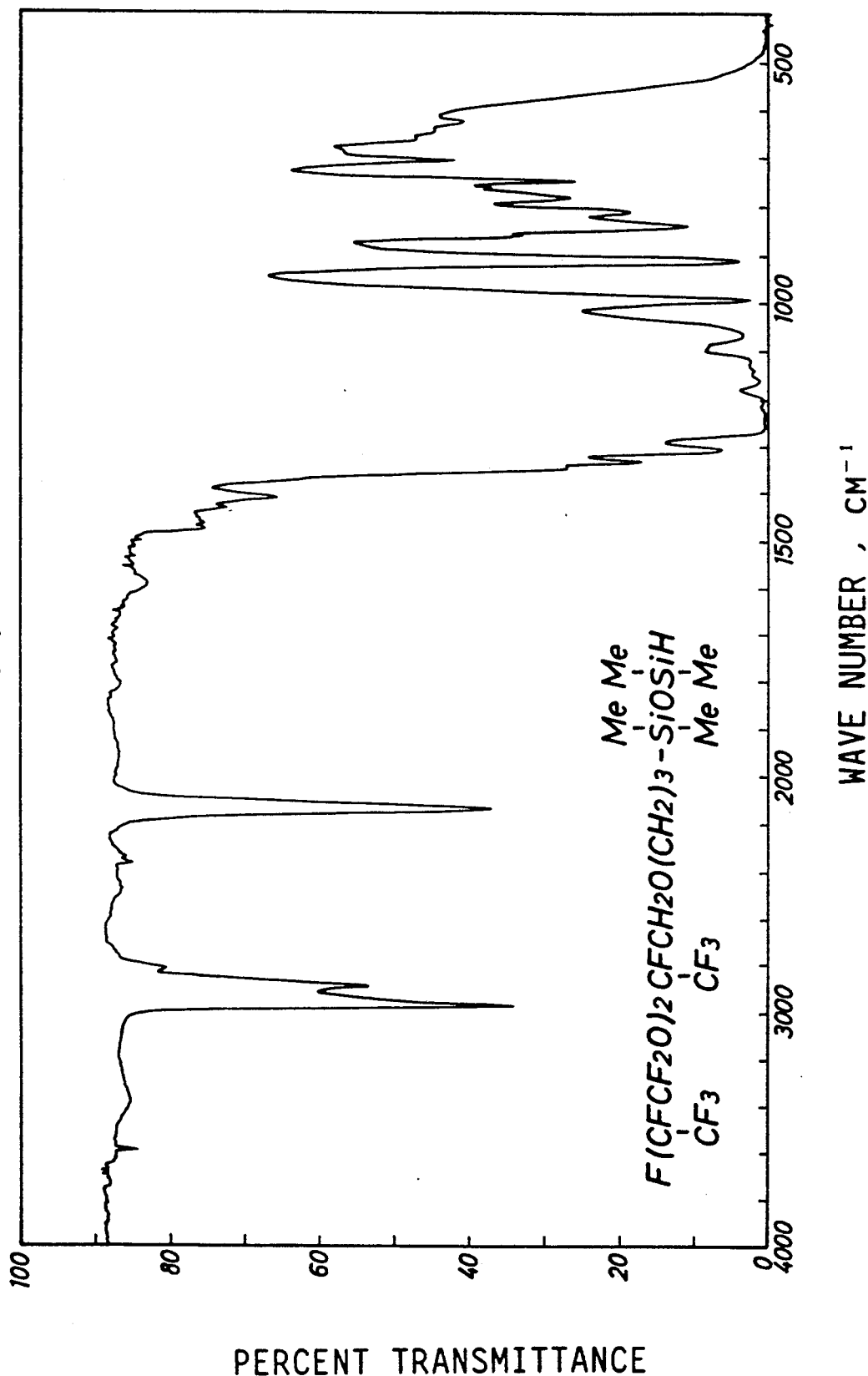
Figure 12:
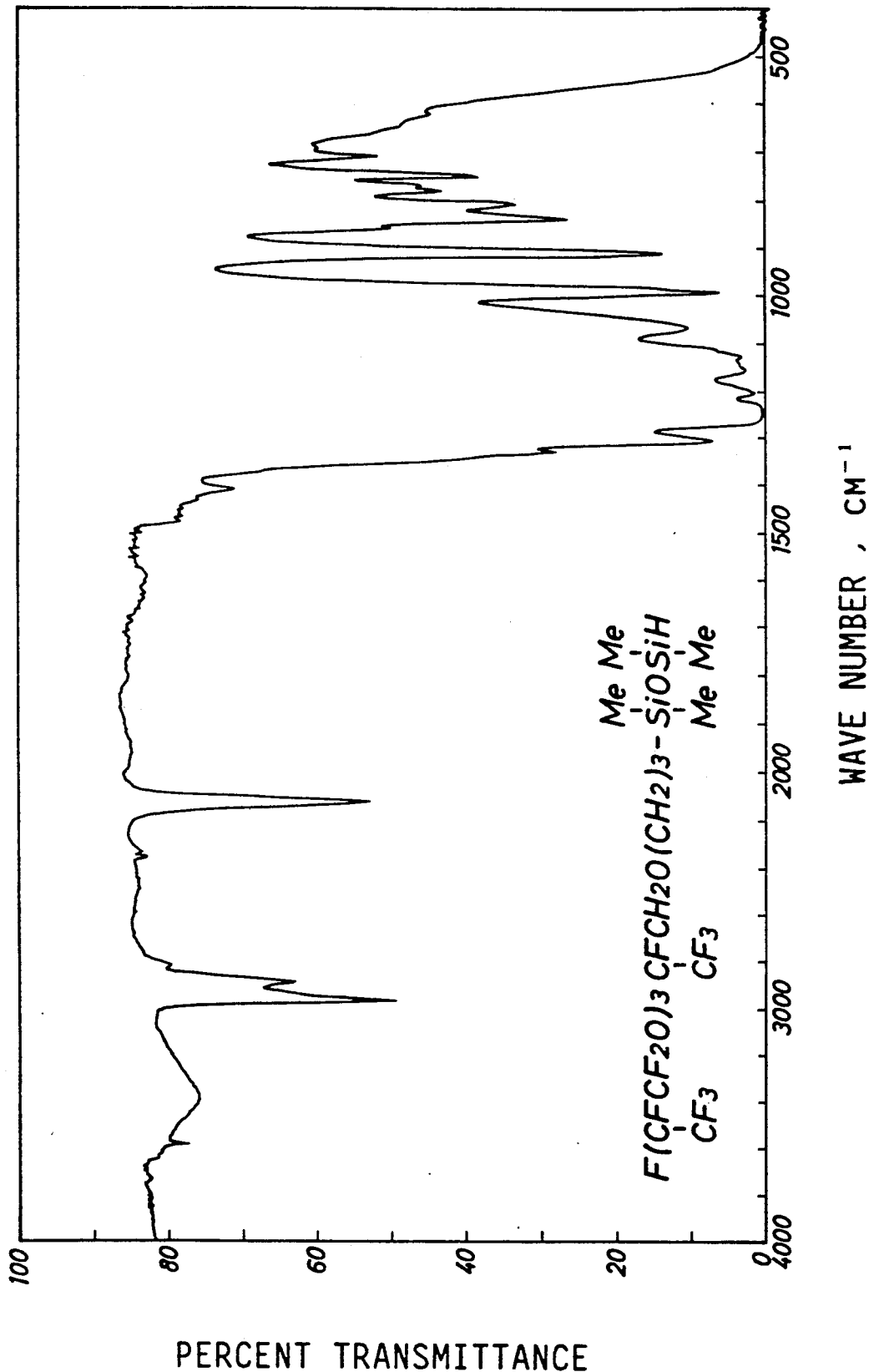
Figure 13:
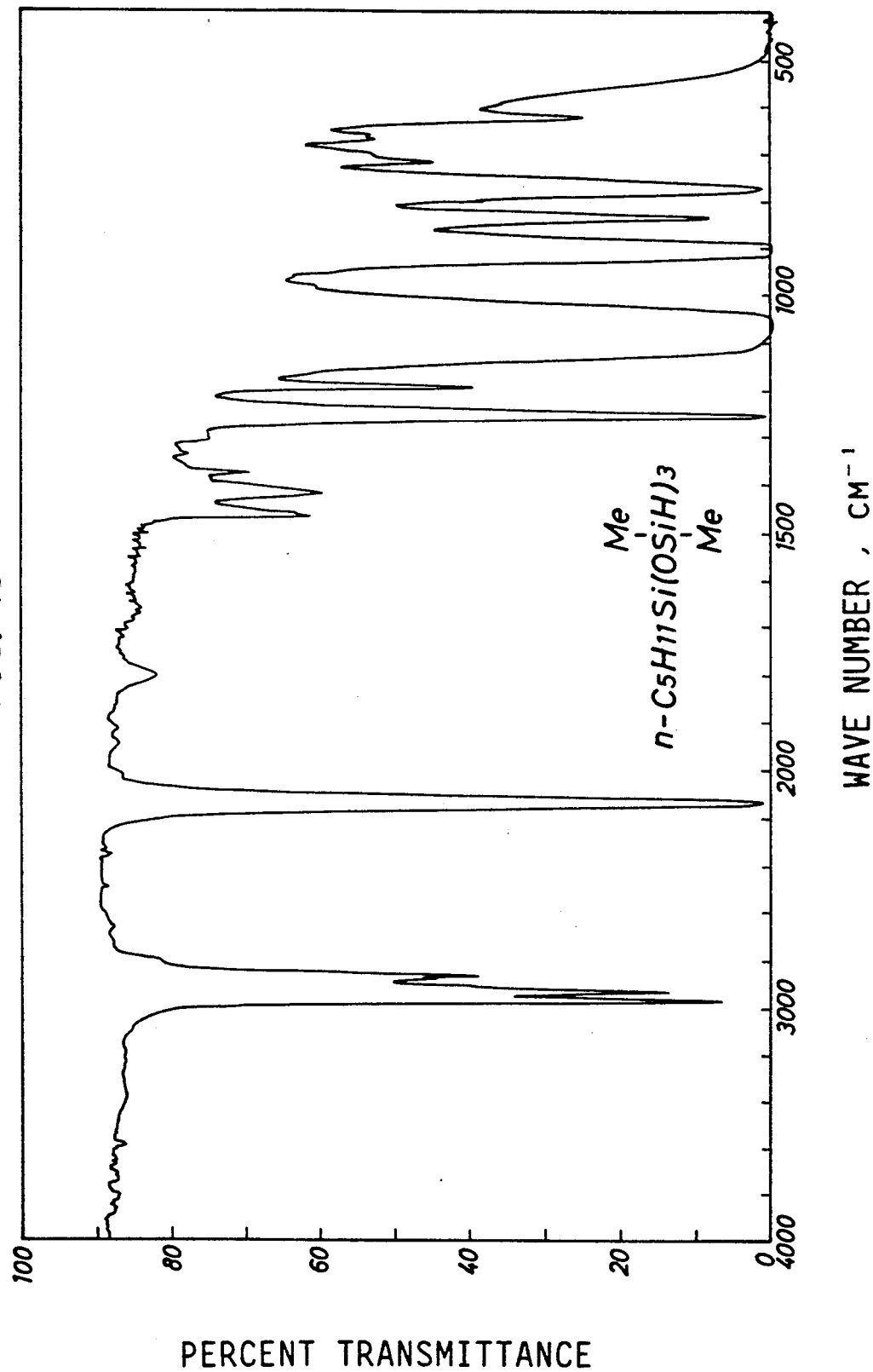
Figure 14:
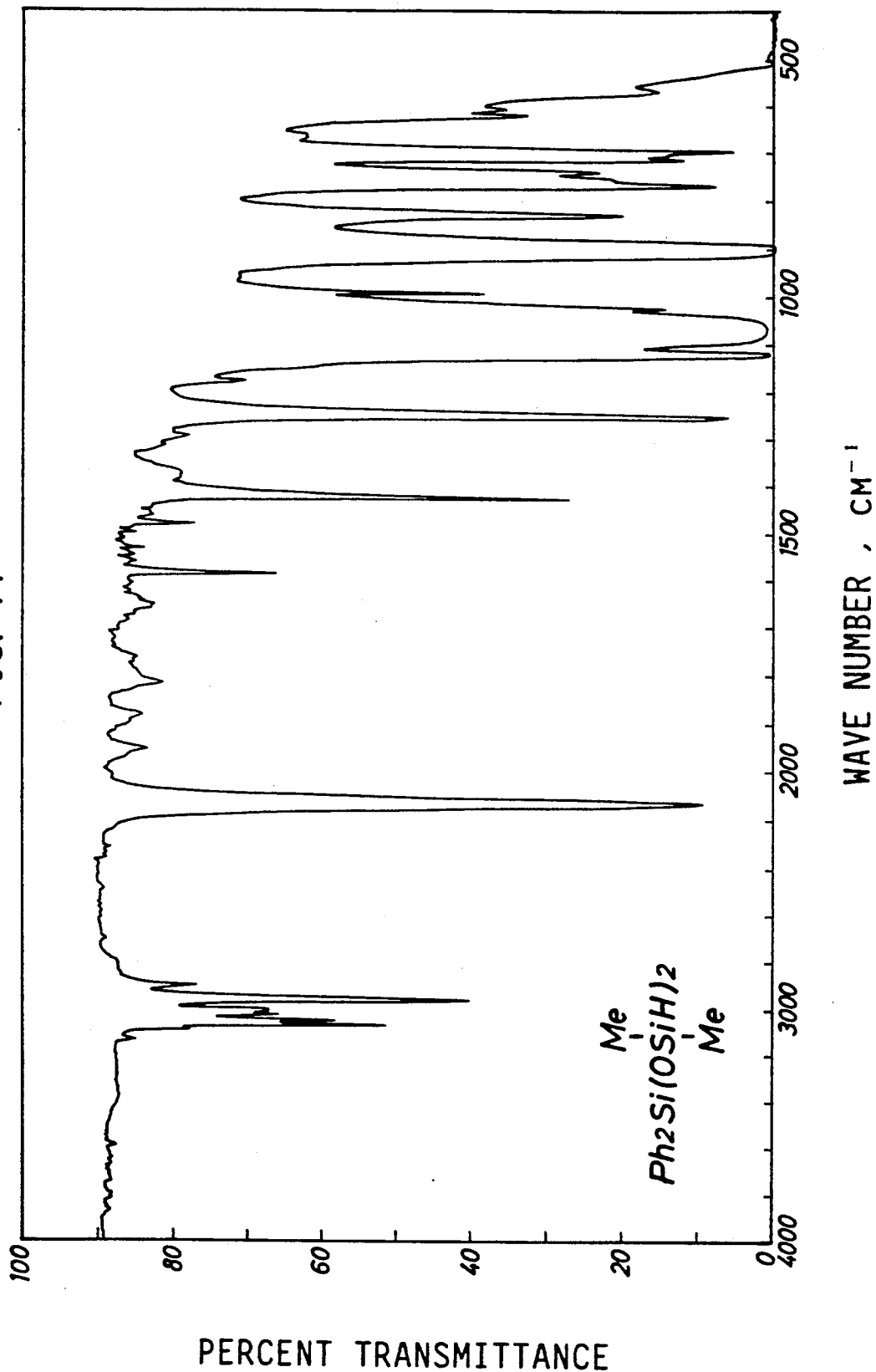
Figure 15:
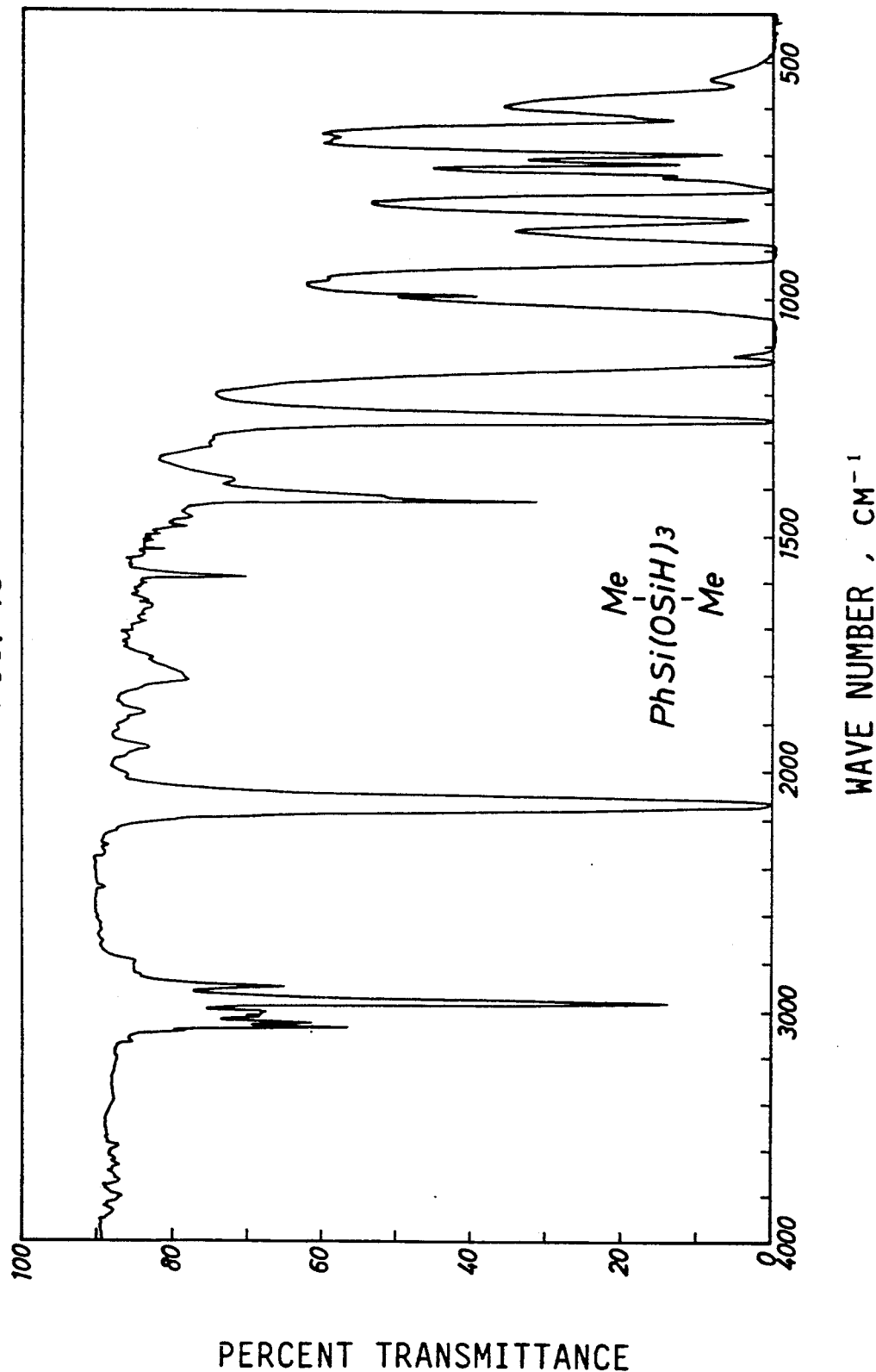
Figure 16:
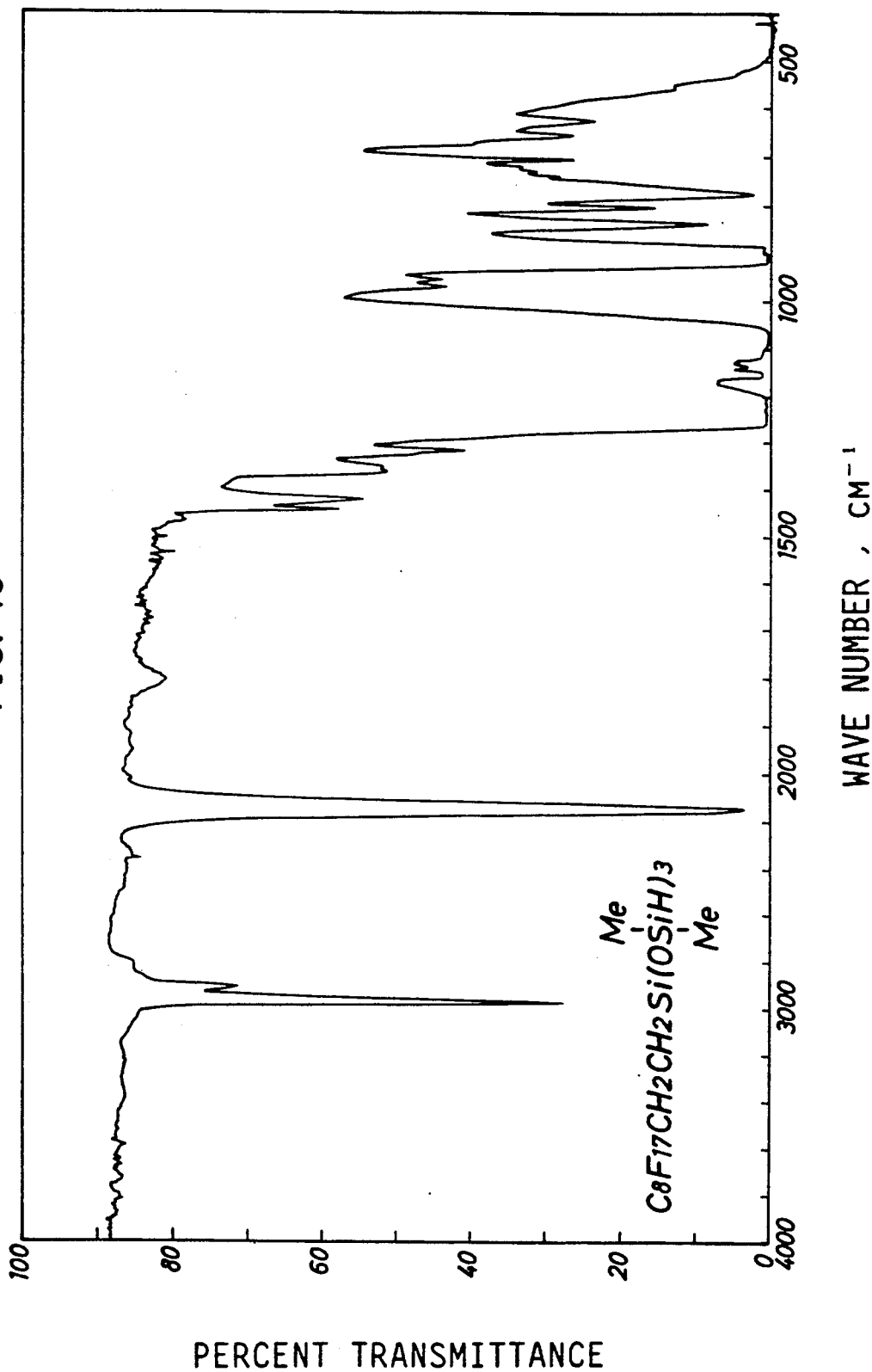
Figure 17:
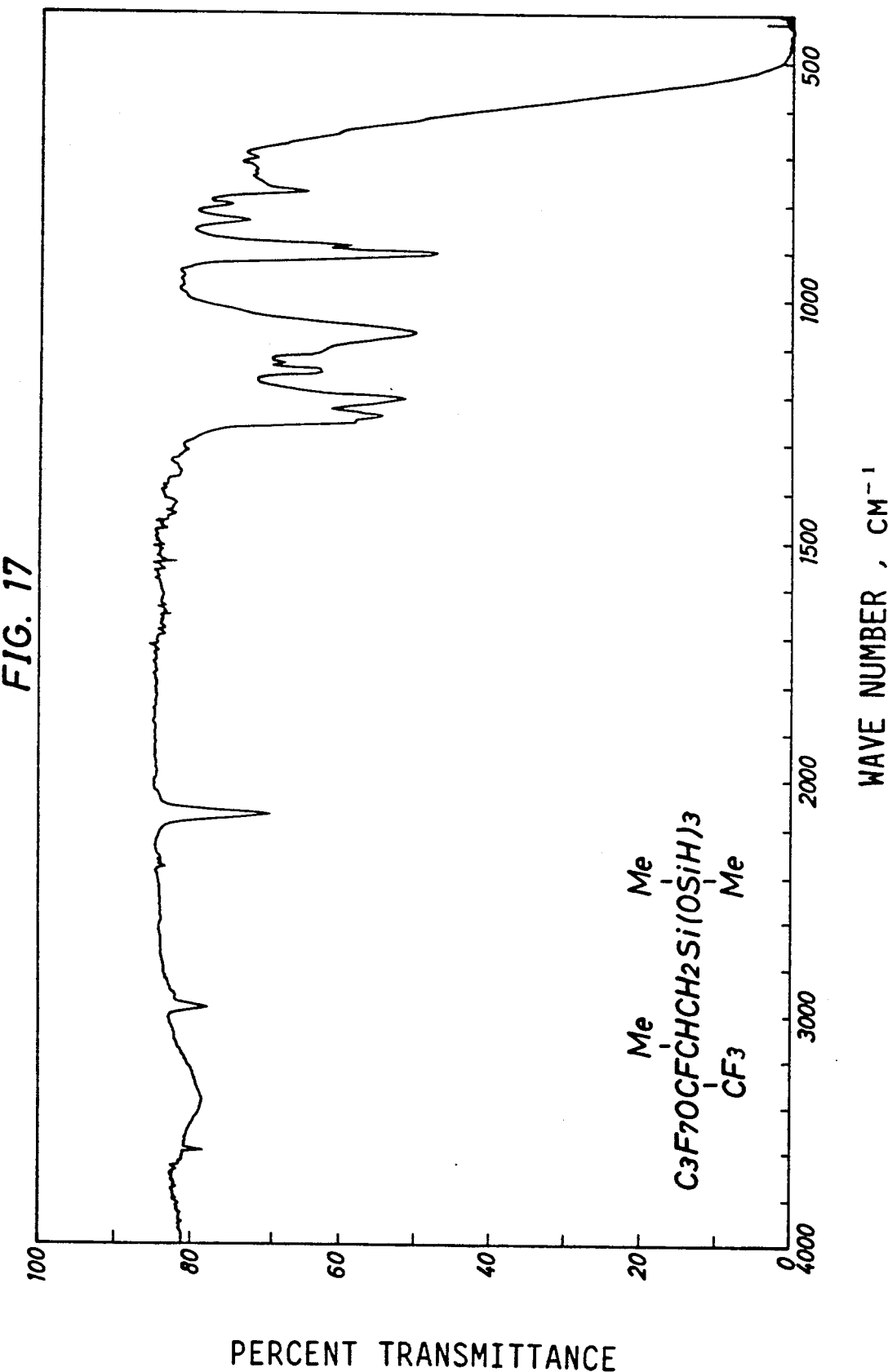
Figure 18:
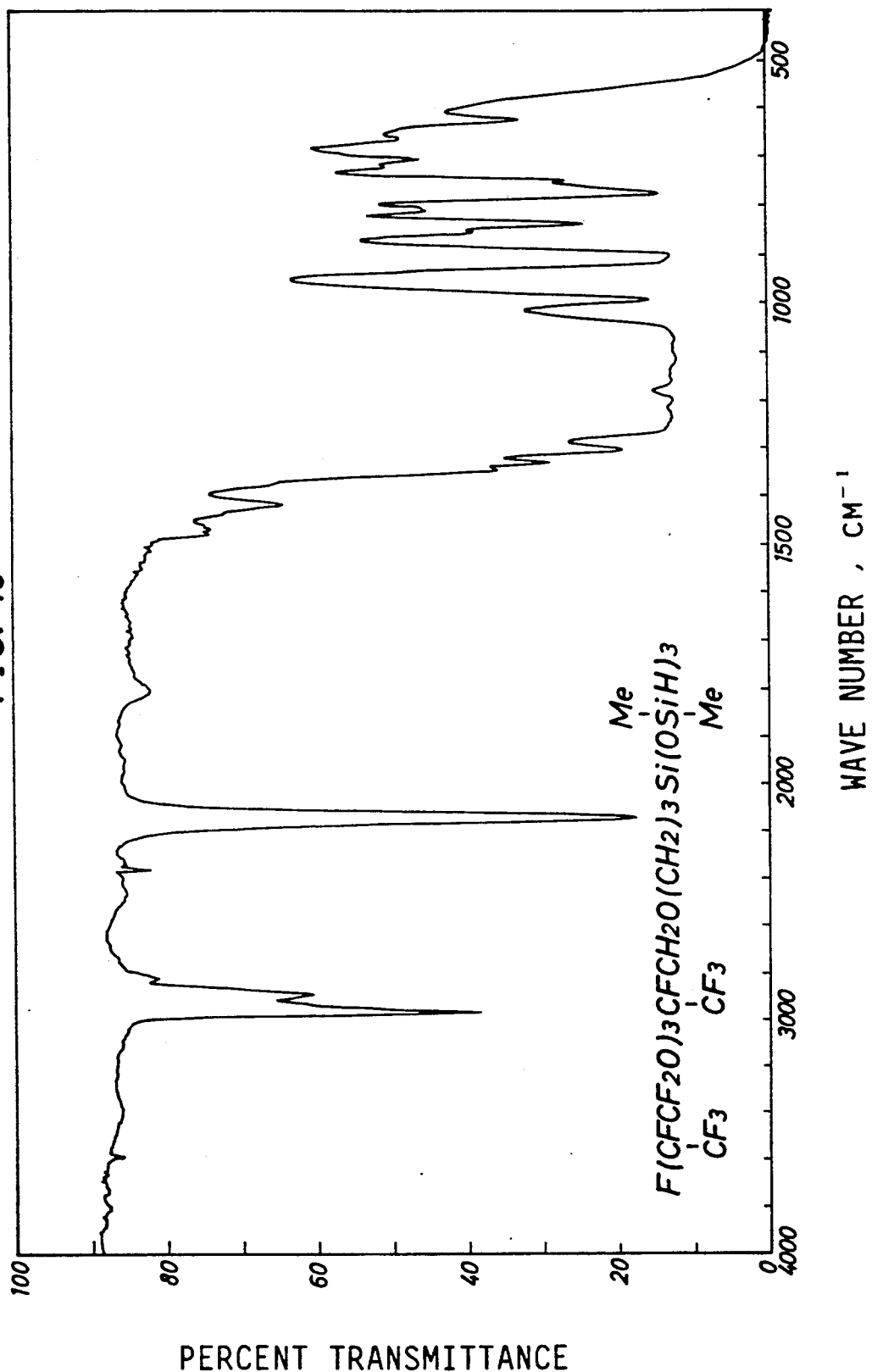

In this invention, a chlorosilane and 1,1,3,3-tetramethyldisiloxane are used as starting material compounds, as mentioned above.

The chlorosilane is represented by the aforementioned general formula (III) or (IV), namely:

$$R_{4-n}SiCl_n \quad (III)$$

$$\underset{RSiCl_m}{\overset{Me_{3-m}}{|}} \quad (IV)$$

In the above general formulas (III) and (IV), n is an integer of 1 to 3, and m is an integer of 1 or 2.

Furthermore, the group R, which may be either identical or different where plural R's exist, represents any one of halogenated hydrocarbon groups, fluorine-substituted ether groups and hydrocarbon groups of at least 2 carbon atoms. Specific examples of the groups R include the followings.

The hydrocarbon groups of at least 2 carbon atoms include, for example, aliphatic hydrocarbon groups such as ethyl, propyl, butyl, hexyl, heptyl, octyl, nonyl, decyl, undecyl, dodecyl, tridecyl, tetradecyl, pentadecyl, etc.; alicyclic hydrocarbon groups such as cyclopentyl, cyclohexyl, cycloheptyl, cyclooctyl, cyclododecyl, etc.; and aromatic hydrocarbon groups such as phenyl, naphthyl, o-methylphenyl, m-methylphenyl, p-methylphenyl, 2,5-dimethylphenyl, 2,3-dimethylphenyl, 3,4-dimethylphenyl, 2,4-dimethylphenyl, benzyl, 1-phenylethyl, 2-phenylethyl, etc.

The halogenated hydrocarbon groups include, for example, chloromethyl, 2-chloroethyl, 3-chloropropyl, and groups represented by the general formula:

$$C_aF_{2a+1}CH_2CH_2-$$

wherein a is an integer of 1, 2, 3, 4, 6 or 8.

The fluorine-substituted ether groups include, for example, fluorine-substituted polyether groups represented by the general formula:

$$R(CFCF_2O)_xCF(CH_2OCH_2)_yCHCH_2-$$
$$\quad\quad\ |\quad\quad\quad\ |\quad\quad\quad\quad\quad\ |$$
$$\quad\quad CF_3\quad\quad\ CF_3\quad\quad\quad\quad R'$$

wherein x is an integer of 1 to 3, y is an integer of 0 or 1, and R' represents a hydrogen atom or the methyl group, etc.

In this invention, the aforementioned chlorosilane and 1,1,3,3-tetramethyldisiloxane are preferably used in such amounts that the total amount, in moles, of the HSi(Me)$_2$O$_{\frac{1}{2}}$ units contained in the disiloxane is in the range from 1 to 5 times, preferably from 1.2 to 1.5 times, the total amount, in moles, of the chlorine atoms contained in the chlorosilane.

Reaction

The reaction between the chlorosilane and the 1,1,3,3-tetramethyldisiloxane is carried out in the presence of water and an acid.

Water, which is necessary for hydrolysis of the chlorosilane, is used preferably in an amount, in moles, of from 1 to 3 times the total amount, in moles, of the chlorine atoms contained in the chlorosilane. If the amount of water is too small, unreacted chlorosilane will be left, whereas if the amount of water is too large, condensation polymerization of the hydrogensiloxane formed may take place to form oligomers.

As the acid, a variety of mineral acids can be used, hydrochrolic acid being particularly preferred. The amount of the acid used is not particularly limited, insofar as the acid acts effectively as a catalyst for the condensation reaction between the silanol, formed through the hydrolysis of chlorosilane, and the 1,1,3,3-tetramethyldisiloxane. Generally, it is preferable that the amount of the acid used is from 1 to 3 parts by weight per 1 part by weight of the water used, at least in the initial stage of the reaction. If the amount of the acid relative to the amount of water is too small, the low acid concentration in the beginning of the reaction causes polycondensation to take place preferentially over the intended reaction, leading to an undesirable result similar to the above. As the reaction progresses, the acid concentration in the reaction mixture is raised by HCl being by-produced through hydrolysis of chlorosilane. If the acid concentration reaches too high a value, Si—H in the hydrogensiloxane formed may be converted into Si—Cl. In order to prevent the conversion, it is preferable to control the amount of the acid in the beginning of the reaction to or below 3 times the total weight of water.

The reaction should be carried out at a temperature of 30° C. or below, preferably in the range from 0° to 20° C. If the reaction temperature exceeds 30° C., the molecules of silanol formed by hydrolysis of chlorosilane may be condensed with each other to form polysiloxane as a by-product, or side reactions such as an equilibration reaction of the hydrogensiloxane formed may take place, resulting in a lowered yield of the intended hydrogensiloxane.

The reaction is carried out by dropping the aforementioned chlorosiloxane into a mixture of 1,1,3,3-tetramethyldisiloxane and an aqueous solution of the acid. The rate of dropping is not particularly limited, insofar as the rate is low enough to prevent the condensation reaction between the molecules of the chlorosilane. Thus, the rate of dropping may be appropriately controlled according to the kind of the substituent groups R in the starting chlorosilane used; taking productivity into consideration, however, it is generally preferable to drop the chlorosilane at such a rate that the whole amount of the chlorosilane is dropped completely in 3 to 6 hours. An addition of the whole amount of the chlorosilane to the mixture at one stroke may increase the possibility of the condensation between the molecules of silanol formed through hydrolysis of the chlorosilane, resulting in a lowered yield of the intended hydrogensiloxane.

In carrying out the aforementioned reaction in this invention, a water-insoluble organic solvent unreactive to hydrogen chloride, hydrogensiloxane, etc. can be used. However, use of such a solvent is not specially required, since the 1,1,3,3-tetramethyldisiloxane and the hydrogensiloxane formed by the reaction serve as solvent. The use of an organic solvent may rather be unadvantageous, from the viewpoint of disposal of waste solvent after the reaction, saving of resources, etc.

In the conventional methods, use of a water-soluble organic solvent such as methanol, ethanol, etc., has been adopted for increasing the rate of hydrolysis. In the process of this invention, on the other hand, the rate of reaction is so high that there is no special need for the use of such a water-soluble organic solvent.

Hydrogensiloxane

After the reaction is finished, a purification treatment is carried out in the usual manner, whereby a hydrogensiloxane represented by the aforementioned general formula (I) or (II), namely:

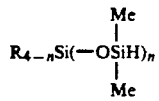
(I)

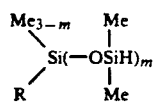
(II)

wherein R, n and m are as defined above, is obtained in high yield. That is, when the chlorosilane of the general formula (III) is used, the hydrogensiloxane of the above formula (I) is obtained, whereas the hydrogensiloxane of the above formula (II) is obtained when the chlorosilane of the general formula (IV) is used.

Of the hydrogensiloxanes, those corresponding to n=1 can be used effectively as a modifier for resins, by making the most of the reactivity of the silicon-hydrogen bond, whereas those comprising a fluorine-containing group as the organic group R are able to provide a mating substrate with the excellent surface characteristics, heat resistance, chemical resistance, etc. possessed by fluorine. Further, those hydrogensiloxanes corresponding to n=2 or 3 are usable as crosslinking agent, vulcanizing accelerator or the like for resins, rubbers, etc.

EXAMPLES

Example 1

A four-necked flask was charged with 134 g (1.0 mole) of 1,1,3,3-tetramethyldisiloxane, 30 g of water and 80 g of concentrated hydrochloric acid, and the mixture was maintained at 5° to 10° C. by cooling with iced water. With sufficient agitation of the contents of the flask, 114 g of methylethyldichlorosilane was dropped into the flask over a period of 4 hours. During the dropwise addition, nitrogen was introduced into the reaction system, while the resultant HCl was removed from the system, and the reaction system was maintained at a temperature of 10° C. or below by utilizing the heat of evaporation of hydrogen chloride.

After the dropwise addition was over, 200 ml of water was added so as to maintain the reaction mixture at a temperature of 20° C. or below. The resultant organic layer was washed twice with water, washed twice with an aqueous 5% solution of $NaHCO_3$ and further washed 5 times with water, followed by drying over $Na_2SO_4$ and distillation under a reduced pressure.

As a distillate at a temperature of 65°–66° C. under a pressure of 50 mmHg, 1,1,3,5,5-pentamethyl-5-ethyltrisiloxane of the formula:

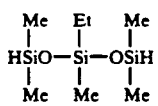

wherein Me represent the methyl group, and Et represents the ethyl group, in this formula and hereinbelow, was obtained in a yield of 71%. The infrared absorption spectrum of the hydrogensiloxane thus obtained is shown in FIG. 1.

Analysis by gas-chromatography (Se-30, 10%, 3 m column) revealed the formation of 1,1,3,5,7,7-hexamethyl-3,5-diethyltetrasiloxane of the formula:

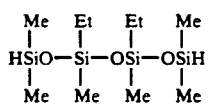

as a by-product in an amount 1/10 in molar basis that of the aimed 1,1,3,5,5-pentamethyl-5-ethyltrisiloxane, but did not show formation of any further longer chain siloxanes.

Examples 2 to 18

Following the procedure of Example 1, various chlorosilanes represented by the general formula (IV) were each reacted with 1,1,3,3-tetramethyldisiloxane, to form hydrogensiloxanes (Examples 2 to 12). Also, a variety of chlorosiloxanes represented by the general formula (III) were used to similarly obtain hydrogensiloxanes (Examples 3 to 18).

The yield, structure, etc. of the hydrogensiloxanes thus obtained are set forth in Tables 1 and 2, and the infrared absorption spectra of the hydrogensiloxanes are shown in FIGS. 2 to 18.

TABLE 1

Synthesis of $\begin{array}{c} Me_{3-m} \\ \diagdown \\ R \end{array} Si(OSiH)_m \begin{array}{c} Me \\ \diagup \\ \diagdown Me \end{array}$

| Example | R | m | Yield (%) | b.p. (°C./mm Hg) |
|---|---|---|---|---|
| 2 | i-Bu | 2 | 76 | 82~84/30 |
| 3 | Ph | 2 | 84 | 76~78/3 |
| 4 | $CF_3CH_2CH_2$ | 2 | 85 | 79~80/57 |
| 5 | $C_4F_9CH_2CH_2$ | 1 | 90 | 65/20 |
| 6 | $C_4F_9CH_2CH_2$ | 2 | 87 | 65~66/5 |
| 7 | $C_6F_{13}CH_2CH_2$ | 1 | 88 | 81~82/11 |
| 8 | $C_8F_{17}CH_2CH_2$ | 1 | 87 | 76~78/3 |

TABLE 1-continued

Synthesis of $RSi(OSiH)_m \begin{matrix} Me_{3-m} Me \\ \diagdown \quad | \\ \diagup \\ Me \end{matrix}$

| Examples | R | m | Yield (%) | b.p. (°C./mm Hg) |
|---|---|---|---|---|
| 9 | $C_8F_{17}CH_2CH_2$ | 2 | 93 | 92~94/4 |
| 10 | $C_3F_7OCFCH_2O(CH_2)_3$<br> $\quad\quad\;\;|$<br> $\quad\quad\;\;CF_3$ | 1 | 92 | 73~75/5 |
| 11 | $F(CFCF_2O)_2CFCH_2O(CH_2)_3$<br>$\quad\;\;|\quad\quad\quad\;\;|$<br>$\quad\;\;CF_3\quad\quad\;\;CF_3$ | 1 | 90 | 100~103/5 |
| 12 | $F(CFCF_2O)_3CFCH_2O(CH_2)_3$<br>$\quad\;\;|\quad\quad\quad\;\;|$<br>$\quad\;\;CF_3\quad\quad\;\;CF_3$ | 1 | 89 | 112~115/3 |

Note:
i-Bu represents the isobutyl group, and Ph the Phenyl group.

TABLE 2

Synthesis of $R_{4-n}Si(OSiH)_n \begin{matrix} Me \\ | \\ | \\ Me \end{matrix}$

| Examples | R | | n | Yield (%) | b.p. (°C./mm Hg) |
|---|---|---|---|---|---|
| 13 | n-$C_5H_{11}$, | — | 3 | 85 | 81~83/3 |
| 14 | Ph, | Ph | 2 | 87 | 121~123/2.4 × 10⁻⁴ |
| 15 | Ph, | — | 3 | 87 | 90~91/2 |
| 16 | $C_8F_{17}CH_2CH_2$, | — | 3 | 85 | 103~104/3.5 |
| 17 | $\quad\quad\;\;Me$<br>$\quad\quad\;\;|$<br>$C_3F_7OCFCH-CH_2,$<br>$\quad\quad\;\;|$<br>$\quad\quad\;\;CF_3$ | — | 3 | 91 | 102~104/15 |
| 18 | $F(CFCF_2O)_3CFCH_2O(CH_2)_3,$<br>$\quad\;\;|\quad\quad\quad\;\;|$<br>$\quad\;\;CF_3\quad\quad\;\;CF_3$ | — | 3 | 89 | 101/4 |

Note:
Ph represents the Phenyl group.

Comparative Example 1

Into a mixture of 1.0 mole of 1,1,3,3-tetramethyl-disiloxane, 30 g of water and 80 g of concentrated hydrochloric acid was dropped 0.8 mole of dimethylchlorosilane, and hydrolysis was carried out at 5° to 10° C.

The hydrogensiloxane of the formula below wherein p is 1 was obtained in a yield of 26%. The hydrogensiloxanes of the formula wherein p is 2 or 3 were obtained in an amount in molar basis of 27% or 7% of the compound of the formula wherein p is 1.

$$\begin{matrix} Me & Me & Me \\ | & | & | \\ HSiO(SiO)_pSiH \\ | & | & | \\ Me & Me & Me \end{matrix}$$

As is apparent from the results, it was confirmed that by-products, i.e., condensates (p≧2) of dimethyldichlorosilane had been formed in considerable amounts.

We claim:

1. A process for producing a hydrogensiloxane represented by the following general formula (I):

$$R_{4-n}Si(-OSiH)_n \begin{matrix} Me \\ | \\ | \\ Me \end{matrix} \quad (I)$$

wherein R represents a group selected from the group consisting of halogenated hydrocarbon groups, fluorine-substituted ether groups and hydrocarbon groups of at least 2 carbon atoms, provided the R groups may be identical or different where plural R's exist, Me represents the methyl group, and n is an integer of 1 to 3, the process comprising reacting a chlorosilane represented by the following general formula (III):

$$R_{4-n}SiCl_n \quad (III)$$

wherein R and n are as defined above,
with 1,1,3,3-tetramethyldisiloxane in the presence of water and an acid at a temperature of 30° C. or below.

2. A process for producing a hydrogensiloxane represented by the following general formula (II):

$$\begin{matrix} Me_{3-m} & Me \\ \diagdown & | \\ Si(-OSiH)_m \\ \diagup & | \\ R & Me \end{matrix} \quad (II)$$

wherein R and Me have the same meanings as defined in respect of the general formula (I) above, and m is an integer of 1 or 2, the process comprising reacting a chlorosilane represented by the following general formula (IV):

$$\begin{matrix} Me_{3-m} \\ | \\ RSiCl_m \end{matrix} \quad (IV)$$

wherein R, Me and m are as defined above,
with 1,1,3,3-tetramethyldisiloxane in the presence of water and an acid at a temperature of 30° C. or below.

3. A process according to claim 1 or 2, wherein the acid comprises hydrochloric acid.

4. A process according to claim 1 or 2, wherein the reaction temperature is in the range from 0° to 20° C.

5. A process according to claim 1 or 2, wherein the 1,1,3,3-tetramethyldisiloxane is used in such an amount that the total amount, in moles, of HSi(Me)₂O₁ units contained in the molecule of the siloxane is 1 to 5 times the total amount, in moles, of chlorine atoms contained in the chlorosilane.

* * * * *